US006555156B1

(12) United States Patent
Loughman

(10) Patent No.: US 6,555,156 B1
(45) Date of Patent: Apr. 29, 2003

(54) PROCESS FOR MAKING ABSORBABLE MICROPARTICLES

(75) Inventor: Thomas Ciaran Loughman, Dublin (IE)

(73) Assignee: Kinerton Limited, Dublin (IE)

( * ) Notice: Subject to any disclaimer, the term of this patent is extended or adjusted under 35 U.S.C. 154(b) by 0 days.

(21) Appl. No.: 09/601,074

(22) PCT Filed: Jan. 25, 1999

(86) PCT No.: PCT/IE99/00007

§ 371 (c)(1), (2), (4) Date: Jul. 26, 2000

(87) PCT Pub. No.: WO99/38535

PCT Pub. Date: Aug. 5, 1999

(51) Int. Cl.[7] .......................... B05D 1/02; A61L 33/12

(52) U.S. Cl. .................... 427/2.14; 427/2.21; 427/212; 427/213.3; 427/213.31; 427/421

(58) Field of Search ............................. 427/2.14, 2.21, 427/212, 213.3, 213.31, 421

(56) References Cited

U.S. PATENT DOCUMENTS

| | | | |
|---|---|---|---|
| 4,767,628 A | 8/1988 | Hutchinson | 424/426 |
| 4,938,763 A | 7/1990 | Dunn et al. | 604/891.1 |
| 5,011,692 A | 4/1991 | Fujioka et al. | 424/426 |
| 5,077,049 A | 12/1991 | Dunn et al. | 424/426 |
| 5,278,201 A | 1/1994 | Dunn et al. | 523/113 |
| 5,366,756 A | 11/1994 | Chesterfield et al. | 427/2.26 |
| 5,385,738 A | 1/1995 | Yamahira et al. | 424/489 |
| 5,612,052 A | 3/1997 | Shalaby | 424/426 |
| 5,665,702 A | 9/1997 | Shalaby et al. | 514/9 |
| 5,672,659 A | 9/1997 | Shalaby et al. | 525/54.1 |
| 5,874,029 A * | 2/1999 | Subramaniam et al. | 264/12 |
| 6,270,700 B1 * | 8/2001 | Ignatious | 264/2.1 |

FOREIGN PATENT DOCUMENTS

| | | | |
|---|---|---|---|
| EP | 0 467 389 A2 | 1/1992 | A61K/9/52 |
| WO | WO 92/11844 * | 7/1992 | A61K/9/26 |
| WO | WO 95/03356 * | 2/1995 | C08G/81/00 |

OTHER PUBLICATIONS

Conti et al., "Use of Polylactic acid for the Preparation of Microparticulate Drug Delivery Systems", Journal of Microencapsulation 9:153–166, 1992, XP002106937.

Corbett et al., "Injectable, Absorbable Gel–formers for Controlled Release of Antibiotics", Database Chemabs Chemical Abstracts Service, Columbus, OH, XP002106938, and Proc. Int. Symp. Controlled Released Bioact. Mater. (1998), $25^{th}$, 38–39 Coden:Pcrymey:Issn: 1022–0178.

Reyderman et al., "Novel Methods of Microparticulate Production: Application to Drug Deliver", Database Chemabs Chemical Abstracts Service, Columbus, OH, XP002106939 and Pharm. Dev. Technol. (1996), 1(3), 223–229 Coden:Pdtefs:Issn: 1083–7450.

* cited by examiner

*Primary Examiner*—Shrive P. Beck
*Assistant Examiner*—Jennifer Kolb Michener
(74) *Attorney, Agent, or Firm*—Fish & Richardson; Brian R. Murrill; Alan F. Feeney

(57) ABSTRACT

The invention pertains to a process for making encased bound microparticles by nebulizing a dispersion of the bound microparticles into a solution of an encasing polymer and into a liquid, non-solvent of said encasing polymer.

15 Claims, No Drawings

PROCESS FOR MAKING ABSORBABLE MICROPARTICLES

TECHNICAL FIELD

This invention pertains to a process for making an encased bound microparticle which is a sustained release complex of one or more peptide, one or more protein or a combination thereof immobilized on an absorbable polymer microparticle having an absorbable encasing polymer. The microparticle complex made by a process of this invention comprises a peptide(s) and/or protein(s) which have at least one amino group and/or at least one carboxyl group per molecule, a solid absorbable polyester micropartide having surface and subsurface carboxylic groups or amino groups in sufficient amounts to bind the peptide(s) and/or protein(s) so that the immobilized peptide(s) or protein(s) represent 0.1% to 30% of the total mass of the microparticle complex which is encased individually or in groups with an absorbable encasing polymer to control the release of the immobilized peptide(s) and/or protein(s).

BACKGROUND ART

Many drug delivery systems have been developed, tested and utilized for the controlled in vivo release of pharmaceutical compositions. For example, polyesters such as poly(DL-lactic acid), poly(glycolic acid), poly(ϵ-caprolactone) and various other copolymers have been used to release biologically active molecules such as progesterone; these have been in the form of microcapsules, films or rods (M. Chasin and R. Langer, editors, Biodegradable Polymers as Drug Delivery Systems, Dekker, N.Y. 1990). Upon implantation of the polymer/therapeutic agent composition, for example, subcutaneously or intramuscularly, the therapeutic agent is released over a specific period of time. Such bio-compatible biodegradable polymeric systems are designed to permit the entrapped therapeutic agent to diffuse from the polymer matrix. Upon release of the therapeutic agent, the poller is degraded in vivo, obviating surgical removal of the implant. Although the factors that contribute to poller degradation are not well understood, it is believed that such degradation for polyesters may be regulated by the accessibility of ester linkages to non-enzymatic autocatalytic hydrolysis of the polymeric components.

For example, Deluca (EPO Publication 0 467 389 A2) describes a physical interaction between a hydrophobic biodegradable polymer and a protein or polypeptide. The composition formed was a mixture of a therapeutic agent and a hydrophobic polymer that sustained its diffusional release from the matrix after introduction into a subject.

Hutchinson (U.S. Pat. No. 4,767,628) controlled the release of a therapeutic agent by uniform dispersion in a polymeric device. It is disclosed that this formulation provides for controlled continuous release by the overlap of two phases: first, a diffusion-dependent leaching of the drug from the surface of the formulation; and second, releasing by aqueous channels induced by degradation of the polymer.

Other in-situ forming biodegradable implants and methods of forming them are described in U.S. Pat. Nos. 5,278,201 ('201 Patent) and U.S. Pat. No. 5,077,049 ('049 Patent), to Dunn et al. The Dunn et al. patents disclose methods for assisting the restoration of periodontal tissue in a periodontal pocket and for retarding a migration of epithelial cells along the root surface of a tooth. The '049 Patent discloses methods which involve placement of an in-situ forming biodegradable barrier adjacent to the surface of the tooth. The barrier is microporous and includes pores of defined size and can include biologically active agents. The barrier formation is achieved by placing a liquid solution of a biodegradable polymer, such as poly(dl-lactide co-glycolide) water-coagulatable, thermoplastic in a water miscible, non-toxic organic solvent such as N-methyl pyrrolidone (i.e., to achieve a typical polymer concentration of about 50%) into the periodontal pocket The organic solvent dissipates into the periodontal fluids and the biodegradable, water coagulatable polymer forms an in-situ solid biodegradable implant The dissipation of solvent creates pores within the solid biodegradable implant to promote cell in growth. The '859 Patent likewise discloses methods for the same indications involving the formation of the biodegradable barrier from a liquid mixture of a biodegradable, curable thermosetting prepolymer, curing agent and water-soluble material such as salt, sugar, and water-soluble polymer. The curable thermosetting prepolymer is described as an acrylic-ester terminated absorbable polymer.

In addition, a number of systems for the controlled delivery of biologically active compounds to a variety of sites are disclosed in the literature. For example, U.S. Pat. No. 5,011,692, to Fujioka et al., discloses a sustained pulsewise release pharmaceutical preparation which comprises drug-containing polymeric material layers. The polymeric material layers contain the drug only in a slight amount, or free of the drug. The entire surface extends in a direction perpendicular to the layer plane and is coated with a polymeric material which is insoluble in water. These types of pulsewise-release pharmaceutical dosages are suitable for embedding beneath the skin.

U.S. Pat. No. 5,366,756, to Chesterfield et al., describes a method of preparing porous bioabsorbable surgical implant materials. The method comprises providing a quantity of particles of bioabsorbable implant material, and coating particles of bioabsorbable implant material with at least one growth factor. The implant can also contain antimicrobial agents.

U.S. Pat. No. 5,385,738, to Yamhira et al., discloses a sustained-release injection system, comprising a suspension of a powder comprised of an active ingredient and a pharmaceutically acceptable biodegradable carrier (e.g., proteins, polysaccharides, and synthetic high molecular weight compounds, preferably collagen, atelo collagen, gelatin, and a mixture thereof) in a viscous solvent (e.g., vegetable oils, polyethylene glycol, propylene glycol, silicone oil, and medium-chain fatty acid triglycerides) for injection. The active ingredient in the pharmaceutical formulation is incorporated into the biodegradable carrier in the following state: (i) the active ingredient is chemically bound to the carrier matrix; (ii) the active ingredient is bound to the carrier matrix by intermolecular action; or (iii) the active ingredient is physically embraced within the carrier matrix.

Moreover, such systems as those previously described in the literature, for example, such as by Dunn, et al. (U.S. Pat. No. 4,938,763), teach in-situ formations of biodegradable, microporous, solid implants in a living body through coagulation of a solution of a polymer in an organic solvent such as N-methyl-2-pyrrolidine. However, the use of solvents, including those of low molecular organic ones, facilitates migration of the solution from the application site thereby causing damage to living tissue including cell dehydration and necrosis. Loss of the solvent mass can lead to shrinkage of the coagulum and separation from surrounding tissue.

U.S. Pat. No. 5,612,052 describes cation-exchanging microparticles made typically of carboxyl-bearing polyester chains onto which basic bioactive agents are immobilized to provide a control release system within an absorbable gel-forming liquid polyester. The contents of U.S. Pat. No. 5,612,052 is incorporated herein by reference. Conjugating carboxylic entities, tonically, with basic polypeptide has been noted in the prior art as described in U.S. Pat. No. 5,672,659 and U.S. Pat. No. 5,665,702. However, these complexes are soluble chemical entities formed by molecularly reacting the individual basic and carboxylic components in their respective solutions to form a well-defined ion-conjugate as a new chemical entity with physicochemical properties.

DISCLOSURE OF INVENTION

The present invention is directed to a process (process A) for making an encased bound micropartide or microparticles wherein the encased bound micropartide or microparticles comprise bound micropartide or microparticles and an absorbable encasing polymer where the bound microparticle or microparticles comprise an absorbable heterochain polymer core and one or more peptide, one or more protein or a combination thereof immobilized on said absorbable heterochain polymer core where each peptide is independently selected from growth hormone releasing peptide (GHRP), luteinizing hormone-releasing hormone (LHRH), somatostatin, bombesin, gastrin releasing peptide (GRP), calcitonin, bradykinin, galanin, melanocyte stimulating hormone (MSH), growth hormone releasing factor (GRF), amylin, tachykinins, secretin, parathyroid hormone (PTH), enkaphelin, endothelin, calcitonin gene releasing peptide (CGRP), neuromedins, parathyroid hormone related protein (PTHrP), glucagon, neurotensin, adrenocorticothrophic hormone (ACTH), peptide YY (PYY), glucagon releasing peptide (GLP), vasoactive intestinal peptide (VIP), pituitary adenylate cyclase activating peptide (PACAP), motilin, substance P, neuropeptide Y (NPY), TSH and analogs and fragments thereof or a pharmaceutically acceptable salt thereof; and where each protein is independently selected from growth hormone, erythropoietin, granulocyte-colony stimulating factor, granulocyte-macrophage-colony stimulating factor and interferons;

said process comprising the steps of:

obtaining a dispersion, where the dispersion comprises solid bound microparticles in a solution of the absorbable encasing polymer, by homogenizing and concurrently dispersing said solid bound microparticles into the solution of an absorbable encasing polymer; and nebulizing said dispersion through a nebulization probe, where said probe has an operating ultrasonic frequency range of 12 kHz to 36 kHz, into a medium, where the medium is a non-solvent of said absorbable encasing polymer, at a flow rate of about 1 ml/min to 15 ml/min.

A preferred process of process A, denoted as process B, is where the medium comprises isopropanol or ethanol.

A preferred process of process B, denoted as process C, is where the solution of the absorbable polymer consists of about 5% to 30% of the absorbable polymer and the temperature of the medium is room temperature to about −80° C.

A preferred process of process A, denoted process D, is where the peptide, peptides, protein or proteins or combination thereof of the bound microparticle comprises 0.1% to 30% of the total mass of the bound microparticle.

A preferred process of D, denoted process E, is where the absorbable polymer core comprises glycolate units and citrate residues wherein the ratio of glycolate units to citrate residues is about 7-1 to about 20-1 or glycolate units and tartrate residues wherein the ratio of glycolate units to tartrate residues is about 7-1 to about 20-1 or glycolate units and malate residues wherein the ratio of glycolate units to malate residues is about 7-1 to about 20-1.

A preferred process of process E, denoted process F, is where the absorbable encasing polymer comprises (a) l-lactide based units and glycolide based units where the ratio of l-lactide based units to glycolide based units is about 60–40 to about 90–10, (b) d,l-lactide based units and glycolide based units where the ratio of d,l-lactide based units to glycolide based units is about 60–40 to about 90–10, (c) d,l-lactide based units, or (d) l-lactide based units and d,l-lactide based units where the ratio of l-lactide based units to d,l-lactide based units is about 80–20.

A preferred process of process F, denoted process G, is where the absorbable encasing polymer constitutes 5 to 70% of the total mass of the encased bound microparticle or microparticles.

A preferred process of process G, denoted process H, is where the absorbable encasing polymer constitutes 20–60% of the total mass of the encased bound microparticle or microparticles.

A preferred process of process H, denoted process I, is where the absorbable encasing polymer constitutes 30–50% of the total mass of the encased bound microparticle or microparticles.

A preferred process of process I, denoted process J, is where the peptide is an LHRH analog.

A preferred process of process J, denoted process K, is where the LHRH analog is p-Glu-His-Trp-Ser-Tyr-D-Trp-Leu-Arg-Pro-Gly-$NH_2$.

A preferred process of process I, denoted process L, is where the peptide is a somatostatin analog.

A preferred process of process L, denoted process M, is where the somatostatin analog is H-β-D-Nal-Cys-Tyr-D-Trp-Lys-Val-Cys-Thr-$NH_2$, where the two Cys are bonded by a disulfide bond.

Another preferred process of process L is where the somatostatin analog is N-hydroxyethylpiperazinyl-acetyl-D-Phe-Cys-Tyr-D-Trp-Lys-Abu-Cys-Thr-$NH_2$ where the two Cys residues are bonded by a disulfide bond.

Yet another preferred process of process L is where the somatostatin analog is N-hydroxyethylpiperazinyl-ethylsulfonyl-Phe-Cys-Tyr-D-Trp-Lys-Abu-Cys-Thr-$NH_2$ where the two Cys residues are bonded by a disulfide bond.

The term “absorbable” as used herein, means a water insoluble material such as a polymer which undergoes chain disassociation in the biological environment to water soluble by-products.

The term “microparticle” as used herein, refers to the particles of absorbable polyester, which are preferably in essentially spherical form.

The term “bound microparticle” as used herein, refers to a microparticle having one or more peptide and/or one or more protein ionically immobilized on the microparticle.

The term “encased microparticle” as used herein, refers to a bound microparticle having a polymer coating, where the polymer coating is not necessarily completely occlusive.

The term “polymer core” as used herein, is another way of referring to microparticles.

The term “encasing polymer” as used herein, refers to the polymer that is used to encase a bound microparticle.

The term “gel-forming liquid polyester” as used herein, refers to materials which absorb solvents such as water, undergo phase transformation and maintain three dimensional networks capable of reversible deformation.

The instant application denotes amino acids using the standard three letter abbreviation known to those skilled in the art, for example Ala=alanine.

A microparticle that is used in a process of the present invention is crystalline and is made of an absorbable polyester, such as polyglycolide having one or more carboxylic groups on the individual chains which results in a sufficient concentration of carboxylic groups on the surface of the microparticle and immediate subsurface of the microparticle to complex and ionically immobilize a peptide(s) and/or a protein(s) having one or more basic groups. Or the carboxylic groups of the polyglycolide can be amidated, for example by a diamine, preferably a primary or secondary amine or a mixture thereof, wherein the amine forms a complex that ionically immobilizes a peptide(s) and/or a protein(s) having one or more acidic groups. Since the surface of the microparticles is not necessarily homogeneous, the term "subsurface" refers to the crevices and the like found on the surface of the microparticles. The bound microparticles provide a means for the controlled release of a peptide(s) and/or protein(s) in a patient. To further control the release of the immobilized peptide(s) and/or protein(s), a process of this invention encases the bound microparticles individually or in groups with an absorbable encasing polymer. The bound microparticles release the peptide(s) and/or protein(s) over a period of about two days to about three months in a patient, preferably about one week to about three months. The encased microparticles release the peptide(s) and/or protein(s) over a period of about three days to six months in a patient, preferably about two weeks to five months.

Typical examples of a peptide that can be immobilized or bound on a microparticle used in this invention include but are not limited to growth hormone releasing peptide (GHRP), luteinizing hormone-releasing hormone (LHRH), somatostatin, bombesin, gastrin releasing peptide (GRP), calcitonin, bradykinin, galanin, melanocyte stimulating hormone (MSH), growth hormone releasing factor (GRF), amylin, tachykinins, secretin, parathyroid hormone (PTH), enkaphelin, endothelin, calcitonin gene releasing peptide (CGRP), neuromedins, parathyroid hormone related protein (PTHrP), glucagon, neurotensin, adrenocorticothrophic hormone (ACTH), peptide YY (PYY), glucagon releasing peptide (GLP), vasoactive intestinal peptide (VIP), pituitary adenylate cydase activating peptide (PACAP), motilin, substance P, neuropeptide Y (NPY), TSH, and analogs and fragments thereof. Examples of proteins that can be immobilized or bound on a microparticle used in this invention are growth hormone, erythropoietin, granulocyte-colony stimulating factor, granulocyte-macrophage-colony stimulating factor and interferons.

A microparticle can be made of a lactide based polymer or a solid semicrystalline polylactone such as polyglycolide which can be formed by ring opening polymerization of acid-bearing hydroxylic initiators such as glycolic, lactic, malic, tartaric, and citric acid. A microparticle used in the present invention can be synthesized according to the following procedure. In a reaction vessel are mixed a lactide based monomer and/or a lactone such as glycolide and an acid initiator such as tartaric acid, malic acid or citric acid. The reaction vessel is warmed to about 35–45° C., preferably 40° C. and put under vacuum for about 20–60 minutes, preferably 30 minutes. The temperature of the reaction vessel is raised to about 105–115° C., preferably 110° C. Once this temperature is reached the vessel is placed under an atmosphere of oxygen-free nitrogen, and the mixture is stirred. Once the mixture melts, a catalytic amount of an organometallic catalyst suitable for ring opening polymerization, such as stannous 2-ethyl-hexanoate solution in a non-protic solvent, such as toluene is added. A vacuum is reapplied for about 30–90 seconds to remove toluene without significant removal of monomer. The temperature of the mixture is raised to about 115–125° C., preferably 120° C. for about 5–10 minutes before further raising it to about 145–150° C. It was kept at this temperature for about 3–5 hours, preferably 4 hours, under constant mechanical stirring.

The resulting polymer is micronized by initially grinding it using a Knife-grinder. The polymer is then micronized in an Aljet Micronizer using a pressurized dry nitrogen stream. The mean particle diameter size is analyzed in a Malvern Mastersizer/E using a volume distribution model and 200/5 cS silicone oil as dispersant.

The polymer is purified and the sodium salt thereof is formed by dispersing the micronized polymer in acetone and placing it in a sonicator, preferably for about 30 minutes. During this time the dispersion was also homogenized at about 8,000–24,000 rpm, preferably 9,500 rpm, using a homogenizer. After this sonication/homogenization step the dispersion is centrifuged at about 3,000–7,000 rpm, preferably 5,000 rpm preferably for about 30 minutes in a centrifuge. The supematant is discarded, the centrifuge cakes re-suspended in fresh acetone, and the sonication/homogenization step repeated. Once the second centrifugation is complete, the supernatant is discarded and the cakes were re-suspended in deionized water. One final sonication/homogenization step is then carried out to remove any remaining acetone and the dispersion is once again centrifuged at about 5,000 rpm for about 30 minutes.

The centrifuge cakes are re-suspended in fresh deionized water and the pH of the dispersion is monitored. Sufficient volumes of a weak base such as 0.2M sodium carbonate solution are added with stirring to raise the pH to between about pH 8 and about pH 9. The dispersions are allowed to stir for about 30 minutes before being vacuum-filtered over filter paper. The filter cakes are rinsed with further deionized water, frozen, and lyophilized.

Purification is monitored by differential scanning calorimetry (DSC) with a heating rate of about 5° C./min to 15° C./min, preferably 10° C./min.

An anion-exchanger microparticle is obtained by taking the cation-exchanger microparticles and incubating it in a hot dilute solution (~80° C.) of a diamine, it is preferred that the amines can be both a primary amine or both a secondary amine or a mixture of a primary and a secondary amine, of known concentration in dioxane or THF under an inert gas such as argon. The concentration of the diamine in dioxane or THF is determined by acidimetry. When the reaction practically ceases to take place, the amidated microparticles are separated by filtration, rinsed with dioxane or THF, and dried under reduced pressure.

A peptide(s) and/or protein(s) can be immobilized on a microparticle according to the following method. The sodium salt of a microparticle is dispersed in solutions containing the free-base of a peptide(s) and/or protein(s) dissolved in water. The dispersions are incubated at room temperature with stirring for about 2 hours before filtering out the bound microparticles. The filter cakes are rinsed with further deionized water, frozen, and lyophilized. Samples are then analyzed for nitrogen by elemental analysis to determine the amount of the peptide(s) and/or protein(s) immobilized.

The size of a microparticle plays a role in the amount of a peptide and/or protein that a microparticle of the instant invention can immobilize. The smaller the size of a microparticle, the more surface area a mass of microparticles and, thus, the more peptide and/or protein can be immobilized per mass of microparticles. Size reduction of the microparticles to micron or sub-micron dimensions can be achieved as described above. The diameter of the microparticles can range in size from about 0.5 $\mu$m to 100 $\mu$m preferably 1 $\mu$m to 15 $\mu$m and more preferably 3 $\mu$m to 10 $\mu$m.

The absorbable encasing polymer can be a crystalline or non-crystalline lactide/glycolide copolymer, amorphous l-lactide/d,l-lactide co-polymer, caprolactone/glycolide copolymer or trimethylene carbonate/glycolide copolymer, that is soluble in conventional organic solvents, such as chloroform, methylene chloride, acetone, acetonitrile, ethyl acetate and ethyl formate or a combination thereof. Non-solvents of such an absorbable encasing polymer include water, low boiling temperature alcohols and hydrocarbons or a combination thereof. The absorbable encasing polymers can be synthesized by catalyzing ring-opening polymerization of lactones, or by polymerization of cyclic monomers such as $\epsilon$-caprolactone, p-dioxanone, trimethylene carbonate, 1,5-dioxepan-2-one or 1,4-dioxepan-2-one in the presence of a chain initiator, such as a hydroxy polycarboxylic acid. Still another method involves reacting an organic polycarboxylic acid with a preformed polyester, which is disclosed in U.S. Pat. No. 5,612,052, the contents of which are incorporated herein by reference.

The encasing of the bound microparticles can be achieved by a process of this invention which involves the use of an ultrasonic atomizer where a dispersion of the bound microparticles in an absorbable encasing polymer solution introduced as micro-droplets into a cooled non-solvent medium (the cooled non-solvent medium is a non-solvent of the absorbable encasing polymer). Bound microparticles are encased with an absorbable encasing copolymer of lactide and glycolide using coagulation of solid microparticles encased in a polymer solution and delivered through an ultrasonic atomizer (nebulizer) into a liquid medium that is a non-solvent for the encasing polymer, but where the liquid medium non-solvent is capable of extracting the solvent of the encasing polymer solution about the encased solid microparticles. The nebulizer probe nebulizes at a frequency of 12 to 36 kHz. It is preferred that a probe be used that can achieve a frequency of about 34 kHz to 36 kHz. The relation between the frequency a probe can generate and its affect on a process of this invention is that a higher frequency allows the process to be able to handle more viscous solutions and also higher flow rates of the dispersion of the bound microparticles in an absorbable encasing polymer solution. Depending on the concentration of the polymer solution for encasing the microparticles, the number of the original bound microparticles in the encased microparticles can vary from 1 to several hundred with an average diameter of an encased microparticle ranging from 0.5 $\mu$m to 100 $\mu$m.

The following method relates to the preparation of encased peptide-loaded and/or protein-loaded (hereinafter peptide-loaded) cation exchangers (CE) by nebulization. The encasing copolymer of interest is dissolved in a solvent, such as either acetonitrile, ethyl acetate or ethyl formate. A sufficient weight of this solution is used for dispersion of the peptide-loaded CE so that the weight ratio of peptide-loaded CE to encasing copolymer ranges from about 30:70 to about 80:20. Dispersion is achieved by high speed homogenization. Peptide loaded cation exchanger is dispersed in acetonitrile or ethyl acetate solution of encasing copolymers. The concentration of encasing copolymer in solution varies from 10% to 25% (W/W) for ethyl acetate and from 12.5% to 30% (W/W) for acetonitrile depending on the particle characteristics desired (morphology, size, specific surface area). The solution is homogenized using a homogenizer, such as an Ultra-turrax T25 (IKA, Staufen, Germany) with dispersing tools attached. A 10-gauge dispersing tool is used for batch sizes of 1 ml to 50 ml while a 25-gauge tool is used for batch sizes of 50 ml to 2.5 L. The rotary speed of these dispersing tools can be varied from 8,000 rpm to 24,000 rpm. The homogenization/dispersion step ensures a uniform dispersal of the polypeptide-loaded cation exchanger in the encasing polymer solution without the need for sonication or vortexing. The dispersion is fed at a flow rate of between 1 ml/min and 10 ml/min to an ultrasonic atomization nozzle with variable frequency—this frequency can be altered from 12 kHz to 36 kHz—higher frequency allows higher flow rates while maintaining particle characteristics. The dispersion is thus nebulized into a collecting sink made up of at least 1 to 10 times excess of a medium such as isopropanol or ethanol (compared to the volume of encasing copolymer solvent used) at room temperature or cooled with sufficient dry-ice pellets (usually 0.5–1 Kg by weight per liter of IPA) so that the temperature of the slurry remains between −50° C. and −80° C. throughout the nebulization. This slurry is stirred at between 300 and 700 rpm depending on its volume. In the case of acetonitrile or ethyl acetate as solvent, the nebulization droplets will freeze immediately on contact with the slurry. Once nebulization is complete the entire dispersion is allowed to thaw of its own accord to between 10° C. and room temperature before vacuum filtering. The filter cakes are rinsed with de-ionized water to remove excess non-solvent. The particles obtained have the appearance of smooth microspheres in the case of a predominantly d,l-lactide encasing copolymer; they appear slightly wrinkled when the encasing copolymer is mainly l-lactide based.

The binding capacity of a microparticle ion-exchanger can be determined as follows. For example, for a cation-exchanger microparticle, available carboxylic groups, in a predetermined mass of the microparticles, are neutralized using cold dilute aqueous sodium carbonate solution of known normality. The neutralized microparticles are isolated by filtration and rinsed thoroughly with cold deionized water and then air dried. The solid microparticles are then incubated in dilute solution of Pilocarpine hydrochloride of known concentration so as to provide a slight excess of the basic drug over that predicted from the binding capacity data. The concentration of the remaining Pilocarpine HCl in the aqueous medium is monitored for a period of time until no significant change in the base pick-up by the microparticles can be recorded. The percent of immobilized base on the microparticles is determined from the exhaustion data and then verified by elemental analysis for nitrogen.

The binding capacity of the anion-exchanger (amidated particles) is determined by (1) elemental analysis for nitrogen and (2) extent of binding to Naproxen by measuring the extent of Naproxen removed from a dilute solution using HPLC. The latter is confirmed by release of the immobilized Naproxen with a dilute sodium hydroxide solution of known concentration.

The encased microparticles made by a process of this invention can be administered to a patient via administration routes well known to those of ordinary skill in the art, such as parenteral administration or oral administration. Preferably it is administered as a powder or a suspension via intranasal route or as an inhalant through the pulmonary system. When it is administered parenterally it is preferable that it is administered as a dispersion in an isotonic aqueous medium or in a non-aqueous, absorbable gel-forming liquid polyester.

The effective dosages of encased microparticles, made by a process of this invention, to be administered to a patient can be determined by the attending physician or veterinarian and will be dependent upon the proper dosages contemplated for the peptide(s) and/or protein(s) and the quantity of the peptide(s) and/or protein(s) immobilized on the microparticles. Such dosages will either be known or can be determined by one of ordinary skill in the art.

MODES FOR CARRYING OUT THE INVENTION

EXAMPLE I

Preparation, Micronization, and Purification of Poly (glycolic acid) Polymers initiated with Citric Acid (PGCA) for use as Cation Exchangers (CE)

Example I(a): 7/1 PGCA—A 500 ml glass reactor was loaded with 242.63 g of glycolide (Purac Biochem, Arkelsedijk, The Netherlands) and 57.37 g of citric acid (Aldrich, Gillingham, Dorset, U.K.). The citric acid had been further dried over silica gel (Fisher Scientific, Loughborough, Leics., U.K.) in an Abderhalden apparatus (Aldrich, St. Louis, Mo., USA). The reactor was immersed in an oil bath at about 40° C. and put under vacuum (0.04 mbar) for about 30 minutes. The bath was then lowered and it's temperature raised to about 110° C. Once this temperature was reached the reactor was placed under an atmosphere of oxygen-free nitrogen and re-immersed. The contents were stirred at about 100 rpm using a Heidolph stirrer (Heidolph Elektro GmbH, Kelheim, Germany). Once the reactor contents melted 1.09 ml of a 0.1M stannous 2-ethylhexanoate solution (Sigma, St. Louis, Mo., USA) in toluene (Riedel de-Haen, Seelze, Germany) was added (stoichiometricratio of 50 ppm). A vacuum was reapplied via a liquid nitrogen trap for about 30 seconds to remove toluene without significant removal of monomer. The oil bath temperature was then raised to about 120° C. for about 5 minutes before further raising it to about 150° C. It was kept at this temperature for about 4 hours under constant mechanical stirring of about 100 rpm. The title polymer was obtained.

Example I(b): 10/1 PGCA—The title polymer was obtained by following the procedure of Example Ia, but using 257.40 g of glycolide, 42.60 g of citric acid and 1.10 ml of a 0.1M stannous 2-ethyl-hexanoate solution in toluene (stoichiometric ratio of 50 ppm).

Example I(c): 15/1 PGCA—15/1 PGCA- A flame-dried resin kettle equipped with a mechanical stirrer and an argon inlet was charged with glycolide (2.586 mole, 300 g), anhydrous citric acid (0.172 mole, 33 g), and stannous octoate (0.2 M in toluene, 862 ml, 0.172 mmole). The polymerization reactor and its contents were purged with dry argon several times. After melting the polymerization charge, the reactants were heated and stirred at about 160° C. until the polymer started to precipitate from the melt. Shortly after partial precipitation, the stirring was terminated and the reaction was continued at about 160° C. for about 2 hours. At the conclusion of the polymerization, the temperature was lowered below 120° C. and excess monomer was removed under reduced pressure. The composition of the isolated polymer was verified using infrared and NMR spectroscopy.

Micronization—Each of the polymers of Examples I(a), I(b) and I(c) were ground initially using a Knife-grinder (IKA, Staufen, Germany). They were then micronized in an Aljet Micronizer (Fluid Energy Aljet, Plumsteadsville, Pa., USA) using a pressurized dry nitrogen stream. Example I(a) had a mean partide diameter size of 24.84 μm by analysis in a Malvern Mastersizer/E (Malvern, Worcs., U.K.) using a volume distribution model and 200/5 cS silicone oil (Dow Corning, Seneffe, Belgium) as dispersant. Examples I(b) and I(c) had mean particle diameter sizes of 4.69 μm and 6.31 μm, respectively, after micronization.

Purification/Sodium Salt Formation—Fifty gram batches of Examples I(a), I(b), and I(c) were dispersed in 2 L of acetone (Riedel de-Haen, Seelze, Germany) and placed in a sonicator (Branson Ultrasonics BV, Soest, The Netherlands) for about 30 minutes. During this time the dispersion was also homogenized at about 9,500 rpm using an Ultra-turrax T25 homogenizer (IKA, Staufen, Germany). After this sonication/ homogenization step the dispersion was centrifuged at about 5,000 rpm for about 30 minutes in a Sorvall centrifuge (Sorvall, Wilmington, Del., USA). The supernatant was discarded, the centrifuge cakes re-suspended in fresh acetone, and the sonication/homogenization step repeated. Once the second centrifugation was complete, the supernatant was discarded and the cakes were re-suspended in deionized water. One final sonication/homogenization step was then carried out to remove any remaining acetone and the dispersion was once again centrifuged at about 5,000 rpm for about 30 minutes.

The centrifuge cakes were re-suspended in fresh deionized water and the pH of the dispersion was monitored. Sufficient volumes of 0.2M sodium carbonate solution were added in each case (with stirring) to raise the pH to between about pH 8 and about pH 9. The dispersions were allowed to stir for about 30 minutes before being vacuum-filtered over a Whatman no.1 (24 cm diameter) filter paper (Whatman Intl. Ltd., Maidstone, Kent, U.K.). The filter cakes were rinsed with further deionized water, frozen, and lyophilized in an Edwards SuperModulyo Lyophilizer (Edwards, Crawley, West Sussex, U.K.).

Purification was monitored by differential scanning calorimetry (DSC) using a TA DSC912S (TA Instruments, New Castle, Del., USA) with a heating rate of 10° C./min. The DSC thermograms obtained in each case did not show any endothermic peak for monomeric glycolide but showed endotherms at 176° C., 178° C., and 180° C. for Examples I(a), I(b), and I(c), respectively.

EXAMPLE II

Preparation of Microparticulate Cation-Exchanger of Glycolide/Malic Acid Copolymer PGMA The title microparticle was synthesized according to the method described in Example I(c) but using glycolide (2.586 mole, 300 g), anhydrous malic acid (0.172 mole, 23 g), and stannous octoate (0.2 M in toluene, 862 ml, 0.172 m mole). Differential Scanning Calorimetry was used to determine the polymer melting temperature (Tm=206° C.).

The solid polymer was ground to achieve average particle diameter of about 125 μm using a Wiley mill. Further reduction of the particle size to about 5–10 μm diameter was achieved using a jet-mill receiving pressurized dry nitrogen. The resulting microparticles were rinsed with acetone to remove trace monomer and low molecular weight oligomers. The product was then dried under reduced pressure at 40° C. until used. The average diameter of the dry microparticle was determined using a particle size analyzer.

EXAMPLE III

Preparation, Micronization, and Purification of a Poly(glycolic acid) Polymer Initiated with Tartaric Acid (PGTA) for Use as a Cation Exchanger (CE)

Example III(a): 10/1 PGTA—A 500 ml glass reactor was loaded with 264.65 g of glycolide (Purac Biochem, Arkelsedijk, The Netherlands) and 34.22 g of L-Tartaric acid (Riedel de-Haen, Seelze, Germany). The tartaric acid had been further dried over silica gel (Fisher Scientific, Loughborough, Leics., U.K.) in an Abderhalden apparatus (Aldrich, St. Louis, Mo.). The reactor was immersed in an oil bath at about 40° C. and put under vacuum (0.04 mbar) for about 30 minutes. The bath was then lowered and it's temperature raised to about 110° C. Once this temperature was reached the reactor was placed under an atmosphere of oxygen-free nitrogen and re-immersed. The contents were stirred at about 100 rpm using a Heidolph stirrer (Heidolph Elektro GmbH, Kelheim, Germany). Once the reactor contents melted 1.14 ml of a 0.1M stannous 2-ethyl-hexanoate solution (Sigma, St. Louis, Mo., USA) in toluene (Riedel de-Haen, Seelze, Germany) was added (stoichiometricratio of 50 ppm). A vacuum was reapplied via a liquid nitrogen trap for about 30 seconds to remove toluene without significant removal of monomer. The oil bath temperature was then raised to about 120° C. for about 5 minutes before further raising it to about 150° C. It was kept at this temperature for about 4 hours under constant mechanical stirring of about 100 rpm. The title polymer was obtained.

Micronization—Example III(a) was ground initially using a Knife-grinder (IKA, Staufen, Germany). It was then micronized in an Aljet Micronizer (Fluid Energy Aljet, Plumsteadsville, Pa., USA) using a pressurized dry nitrogen stream. This gave a mean particle diameter of 12.42 μm by analysis in a Malvern Mastersizer/E (Malvern, Worcs., U.K.) using a volume distribution model and 200/5 cS silicone oil (Dow Coming, Seneffe, Belgium) as dispersant.

Purification/Sodium Salt Formation—A 50 g batch of Example III(a) was dispersed in 2 L of acetone (Riedel de-Haen) and placed in a sonicator (Branson Ultrasonics BV, Soest, The Netherlands) for about 30 minutes. During this time the dispersion was also homogenized at about 9,500 rpm using an Ultra-turrax T25 homogenizer (IKA, Staufen, Germany). After this sonication/homogenization step the dispersion was centrifuged at about 5,000 rpm for about 30 minutes in a Sorvall centrifuge (Sorvall, Wilmington, Del., USA). The supernatant was discarded, the centrifuge cakes re-suspended in fresh acetone, and the sonication/homogenization step repeated. Once the second centrifugation was complete, the supematant was discarded and the cakes were re-suspended in deionized water. One final sonication/homogenization step was then carried out to remove any remaining acetone and the dispersion was once again centrifuged at about 5,000 rpm for about 30 minutes.

The centrifuge cakes were resuspended in fresh de-ionized water and the pH of the dispersion was monitored. A sufficient volume of 0.2M sodium carbonate solution was added to raise the pH to between about pH 8 and about pH 9. The dispersion was allowed to stir for about 30 minutes before being vacuum-filtered over a Whatman no.1 (24 cm diameter) filter paper (Whatman Intl. Ltd., Maidstone, Kent, U.K.). The filter cake was rinsed with further deionized water, frozen, and lyophilized in an Edwards SuperModulyo Lyophilizer (Edwards, Crawley, West Sussex, U.K.).

Purification was monitored by DSC using a TA DSC912S (TA Instruments New Castle, Del., USA) with a heating rate of about 10° C./min. The DSC thermogram obtained did not show any endothermic peak for monomeric glycolide but showed an endotherm at 181° C.

Example III(b): 15/1 PGTA—The tide polymer was synthesized according to the procedure described for Example I(c) but using glycolide (2.586 mole, 300 g), anhydrous tartaric acid (0.172 mole, 26.8 g) and stannous octoate (0.2 M in toluene, 862 ml, 0.0172 mmole). Differential Scanning Calorimetry was used to determine the polymer melting temperature (Tm=204° C.).

The solid polymer was ground to achieve average particle diameter of about 125 μm using a Wiley mill. Further reduction of the particle size to about 5–10 μm diameter was achieved using a jet-mill receiving pressurized dry nitrogen. The resulting microparticles were rinsed with acetone to remove trace amounts of monomer and low molecular weight oligomers. The product was then dried under reduced pressure at about 40° C. until used. The average diameter of the dry microparticle was determined using a particle size analyzer.

EXAMPLE IV

Preparation of Polyglycolide-based Microparticulate Anion-Exchanger (AE-1)

The preparation of an anion-exchanger is achieved in two steps. First, low molecular weight poly glycolide is prepared using a similar procedure in Example I(c), but using the following polymerization charge: glycolide (1 mole, 116 g), 1,3 propanediol as an initiator (30 mmole, 2.22 g) and stannous octoate (0.03 mmole). The size reduction and purification of the polymer are then conducted as also described in Example I(c). In the second step, the practically non-ionic microparticles are incubated in hot dilute solution (~80° C.) of a diamine, for example hexanediamine of known concentration in dioxane under argon. The concentration of the diamine in dioxane is determined by acidimetry. When the reaction practically ceases to take place, the amidated microparticles are separated by filtration, rinsed with dioxane, and dried under reduced pressure. The binding capacity of the anion-exchanger (amidated particles) is determined by (1) elemental analysis for nitrogen and (2) extent of binding to Naproxen by measuring the extent of drug removed from a dilute solution using HPLC. The latter is confirmed by release of the immobilized Naproxen with a dilute sodium hydroxide solution of known concentration.

EXAMPLE V

Preparation of Poly(lactide co-glycolide) Copolymers Initiated with Propanediol (PLGPD) for Use as Encasing Materials Example V(a): 75/25 P(I)LGPD—A 500 ml glass reactor was loaded with 235.01 g of l-lactide(Purac Biochem, Arkelsedijk, The Netherlands), 63.09 g of glycolide (Purac Biochem, Arkelsedijk, The Netherlands) and 1.90 g of propanediol (Riedel de-haen, Seelze, Germany) and then 3.96 ml of a 0.1M stannous 2-ethyl-hexanoate solution (Sigma, St. Louis, Mo., USA) in toluene (Riedel de-haen, Seelze, Germany) was added (stoichiometric ratio of 200 ppm). After drying under vacuum for about one hour to remove the toluene, the reactor was placed under an atmosphere of oxygen-free nitrogen and immersed in an oil bath preheated at about 160° C. The reactor contents were stirred at about 100 rpm with a Heidolph stirrer (Heidolph Elektro GmbH, Kelheim, Germany). Once the contents had melted the temperature was increased to about 180° C. and maintained at this level for about 3 hours. An amorphous copolymer was obtained. The copolymer was found to have a molecular weight (MW) of about 12,500 g/mol by gel permeation chromatography (GPC) on a Waters 510 Pump, Waters 410 Differential Refractometer (Waters, Milford, Mass., USA) with light-scattering detection on a Wyatt Minidawn Light Scattering Detector (Wyatt Technology Corporation, Santa Barbara, Calif., USA).

Example V(b): 90/10 P(I)LGPD—The title product was synthesized according to the procedure of Example V(a) but using 274.31 g of l-lactide, 24.55 g of glycolide, 1.14 g of propanediol and 3.89 ml of a 0.1M stannous 2-ethylhexanoate solution in toluene (stoichiometric ratio of 200 ppm). A crystalline copolymer was obtained. The copolymer was found to have a molecular weight of about 20,650 g/mol by GPC.

Example V(c): 90/10 P(d,l)LGPD—The title product was obtained by following the procedure of Example V(a) but using 274.31 g of d,l-lactide, 24.55 g of glycolide, 1.14 g of propanediol and 3.86 ml of a 0.1 M stannous 2-ethyl-hexanoate solution in toluene (stoichiometric ratio of 200 ppm). An amorphous copolymer was obtained. The copolymer was found to have a molecular weight of about 20,650 g/mol by GPC.

Example V(d): Poly(l-lactide co-d,l-lactide) copolymer initiated with Propanediol (PLGPD) for use as Coating Material, 80/20 P(l)L(d,l)LPD The title product was obtained by following the procedure of Example V(a) but using 239.09 of l-lactide, 59.77g of d,l-lactide (Purac Biochem, Arkelsedijk. The Netherlands) and 1.14 g of propanediol and 3.96 ml of a 0.1M stannous 2-ethyl-hexanoate solution in toluene was added (stoichiometric ratio of 200 ppm). An amorphous copolymer was obtained. The copolymer was found to have a molecular weight (Mw) of 22,320 g/mol by GPC. It showed a glassy transition at 48° C. by DSC.

Purification—Examples V(a), V(b), and V(c) were each washed by nebulization of a 30% (W/W) solution in acetonitrile (Labscan, Dublin, Ireland) at 8 ml/min into deionized water cooled to about 20° C. in a 6 L jacketed reactor linked to a circulation bath and stirred at about 350 rpm with a Heidolph stirrer (Heidolph Elektro GmbH, Kelheim, Germany). The solutions were fed to a Vibra-Cell VC 50 Atomization nozzle (Bioblock, Illkirch, France) using a Masterflex pump (Cole Parmer Instrument Co., Niles, Ill., USA) and nebulization was achieved using a sonication frequency of 12 kHz. The dispersions obtained were filtered over Whatman No.1 (24 cm diameter) filter papers (Whatman Intl. Ltd., Maidstone, Kent, U.K.) and the filter cakes were rinsed with deionized water, frozen, and lyophilized in an Edwards SuperModulyo Lyophilizer (Edwards, Crawley, West Sussex, U.K.).

Purity was confirmed by DSC using a TA DSC912s (TA Instruments, New Castle, Del., USA) with a heating rate of 10° C./min which showed glass transitions (Tg) at 44° C., 49° C., 45° C. and 48° C. for Examples V(a), V(b), V(c) and V(d), respectively.

EXAMPLE VI

Preparation of Peptide-Loaded Cation Exchangers

Example VI(a): Loading with Peptide A (p-Glu-His-Trp-Ser-Tyr-D-Trp-Leu-Arg-Pro-Gly-$NH_2$, an LHRH analog)—Four grams of each of the sodium salts of Examples I(a), I(b), I(c) and II(a) were dispersed in solutions containing 1.33 g of the free-base of Peptide A (Kinerton Ltd., Dublin, Ireland) dissolved in 70 ml of deionized water. The dispersions were incubated at room temperature with stirring for about 2 hours before filtering over a 9 cm diameter Whatman No.1 filter paper (Whatman Intl. Ltd., Maidstone, Kent, U.K.). The filter cakes were rinsed with further deionized water, frozen, and lyophilized in an Edwards SuperModulyo (Edwards, Crawley, West Sussex, U.K.). Samples were then analyzed for nitrogen by elemental analysis to determine the amount of Peptide A bound. The following results were obtained:

| Example | CE Ex.-# | CE Polymer | wt % Peptide A Bound |
|---|---|---|---|
| VI(a)(i) | I(a) | 7/1 PGCA | 24.52% |
| VI(a)(ii) | I(b) | 10/1 PGCA | 12.60% |
| VI(a)(iii) | I(c) | 15/1 PGCA | 19.29% |
| VI(a)(iv) | III(a) | 10/1 PGTA | 17.60% |

Example VI(b): Loading with Peptide B (H-β-D-Nal-Cys-Tyr-D-Trp-Lys-Val-Cys-Thr-$NH_2$, the two Cys are bonded by a disulfide bond, a somatostatin analogue)—Following the procedure of Example VI(b) and using 4 g of each of the sodium salts of Examples I(a), I(b), I(c) and II(a) and 1.33 g of the free-base of Peptide B (Kinerton Ltd., Dublin, Ireland) bound microparticles of Examples I(a), I(b) and I(c) with peptide B immobilized thereon were obtained. Samples were analyzed for nitrogen content by elemental analysis to determine the amount of Peptide B bound. The results obtained are shown below:

| Example | CE Ex.-# | CE Polymer | wt % Peptide B Bound |
|---|---|---|---|
| VI(b)(i) | I(a) | 7/1 PGCA | 25.20% |
| VI(b)(ii) | I(b) | 10/1 PGCA | 13.10% |
| VI(b)(iii) | I(c) | 15/1 PGCA | 19.64% |
| VI(b)(iv) | III(a) | 10/1 PGTA | 14.23% |

EXAMPLE VII

Preparation of Encased Polypeptide-Loaded Cation Exchangers by Nebulization

Polypeptide-loaded cation exchangers were dispersed in acetonitrile (Labscan, Dublin, Ireland) solutions of encasing copolymers, indicated below. This dispersal was achieved by homogenizing with an Ultra-turrax T25 (IKA, Staufen, Germany) at about 9,500 rpm for about 5 minutes. The concentration of the encasing copolymer/acetonitrile solutions ranged from 12.5% to 25% (W/W) and the ratio of encasing copolymer to polypeptide-loaded cation exchanger ranged from 1:1 to 1.3:1 by weight.

After dispersal, the dispersion was fed to a Vibra-Cell VC50 atomization nozzle (Bioblock, Illkirch, France) with a sonication frequency of 16 kHz using a ceramic piston pump (FMI, Oyster Bay, N.Y., USA) set at 2 ml/min flow rate. Upon reaching the nozzle the dispersion was nebulized into isopropyl alcohol (IPA) (Labscan, Dublin, Ireland) cooled to about −80° C. by the addition of dry-ice pellets (A.I.G., Dublin, Ireland). The IPA acted as a collecting non-solvent and was stirred at about 300 rpm using a Heidolph stirrer (Heidolph Elektro GmbH, Kelheim, Germany). Once nebulization was complete the entire dispersion was allowed to thaw to a temperature between about 10° C. and about room temperature. The encased microparticles were then recovered by vacuum filtration over a Whatman No.1 filter paper (Whatman Intl. Ltd., Maidstone, Kent, U.K.). The filter cake was rinsed with deionized water, frozen and lyophilized in an Edwards SuperModulyo lyophilizer (Edwards, Crawley, West Sussex, U.K.). The resulting encased microparticles were analyzed for size using the Malvern Mastersizer/E (Malvern, Worcs., U.K.) and 1% Tween 20 in water as a dispersant. The encased microparticles were also analyzed for nitrogen content by elemental analysis to determine peptide content. The table below represents the various encasing experiments carried out:

| Ex. # | Peptide-Loaded CE: Ex-# | Encasing Copolymer Ex-# | Conc. (W/W) of Encasing Copolymer in Acetonitrile | Encasing Copolymer Peptide-loaded CE | Mean Particle Diameter | wt. % Peptide Loading |
|---|---|---|---|---|---|---|
| VII(a) | VI(a)(ii) | V(a) | 24.31% | 1:1 | 122.14 μm | 5.38% Peptide A |
| VII(b) | VI(a)(ii) | V(b) | 22.41% | 1:1 | 120.15 μm | 6.38% Peptide A |
| VII(c) | VI(a)(iii) | V(b) | 12.5% | 1:1 | 79.30 μm | 7.76% Peptide A |
| VII(d) | VI(a)(iii) | V(c) | 12.5% | 1:1 | 77.85 μm | 8.93% Peptide A |
| VII(e) | VI(a)(iv) | V(c) | 14.95% | 1:1 | 136.74 μm | 8.75% Peptide A |
| VII(f) | VI(a)(i) | V(c) | 14.92% | 1.27:1 | 80.59 μm | 10.31% Peptide A |
| VII(g) | VI(b)(ii) | V(a) | 25.37% | 1:1 | 140.58 μm | 2.63% Peptide B |
| VII(h) | VI(b)(ii) | V(b) | 20% | 1.15:1 | 96.77 μm | 5.98% Peptide B |
| VII(i) | VI(b)(iii) | V(b) | 12.5% | 1:1 | 102.56 μm | 7.69% Peptide B |
| VII(j) | VI(b)(iii) | V(c) | 12.5% | 1:1 | 83.72 μm | 7.90% Peptide B |
| VII(k) | VI(b)(iv) | V(c) | 14.95% | 1:1 | 135.14 μm | 6.69% Peptide B |
| VII(I) | VI(b)(i) | V(c) | 14.92% | 1.26:1 | 123.18 μm | 10.11% Peptide B |

All samples were sieved over a 180 μm sieve (Bioblock, Illkirch, France) prior to in vivo and/or in vitro testing.

A bound microparticle or encased microparticle can be tested in vitro to assess the release rate of a bound peptide or bound protein by the following method. An aliquot of a bound microparticle or encased microparticle having a mass of about 50 mg is placed in a continuous flow-cell system where a buffered phosphate solution at about pH 7.2 and at about 37° C. flow across the entire mass of the bound microparticles or encased microparticles at a rate of about 45 ml/hr. Samples of the buffer containing the released drug are collected at about 4° C. and analyzed for the peptide or protein concentrations at 1- or 2-day intervals. The release profile of each microparticle is determined over a period of 2 weeks.

A bound microparticle or encased microparticle can be tested to assess the release rate of a bound peptide or bound protein in an in vivo system by the following method. Samples are administered to male Wistar rats (Bioresources, Trinity College, Dublin, Ireland) by intramuscular injection to the thigh. The suspension medium consists of 3% carboxymethylcellulose and 1 % Tween 20 in saline solution. For Peptide A-loaded samples the effective equivalent dose is 40 μg/Kg/day. The dose for Peptide B-loaded samples is 1 mg/Kg/day. Samples are taken by cardiac puncture and the plasma peptide levels are monitored by radioimmunoassays (RIA) specific for Peptide A and Peptide B. In the case of Peptide A-loaded samples (Peptide A is an LHRH analog), a testosterone RIA is also used to monitor testosterone suppression. As an alternative to the suspension medium, gel-formers can be used in certain cases. The results are shown in Tables A and B, below.

TABLE A

| Peptide A Examples | Peptide A (>150 pg/ml) Days | Testosterone (<1 ng/ml) Days |
|---|---|---|
| VII(a) | 20 | 21 |
| VII(b) | 10 | 10 |

TABLE A-continued

| Peptide A Examples | Peptide A (>150 pg/ml) Days | Testosterone (<1 ng/ml) Days |
|---|---|---|
| VII(c) | 2 | 11 |
| VII(d) | 2 | 11 |
| VII(e) | 2 | 13 |
| VII(f) | 2 | 16 |
| VII(a) in gel-former | 25 | 44 |

TABLE B

| Peptide B Examples | Peptide B (>1000 pg/ml) Days |
|---|---|
| VII(g) | Not tested |
| VII(h) | Not tested |
| VII(i) | Not tested |
| VII(j) | 15 |
| VII(k) | 10 |
| VII(l) | 10 |

EXAMPLE VIII

VIII(a): Nebulization Using Acetonitrile as Solvent and Room Temperature IPA as Non-solvent About 1.06 g of the cation exchanger of Example I(c) (not bound to polypeptide) was dispersed in a 25.24% (W/W) solution of encasing copolymer of Example V(a) in acetonitrile (Labscan, Dublin, Ireland) such that the ratio of cation exchanger to encasing copolymer was about 1.03:1 by weight. This dispersal was achieved by homogenizing with an Ultra-turrax T25 (IKA, Staufen, Germany) at about 9,500rpm for about 5 minutes.

After dispersal, the dispersion was fed to a Vibra-Cell VC50 atomization nozzle (Bioblock, Illkirch, France) with a sonication frequency of 16 kHz using a ceramic piston pump (FMI, Oyster Bay, N.Y., U.S.A.) set at 2 ml/min flowrate. Upon reaching the nozzle the dispersion was nebulized into IPA (Labscan, Dublin, Ireland) at room temperature (17 to 22° C.). This IPA acted as a collecting non-solvent and was stirred at about 300 rpm using, a Heidolph stirrer (Heidolph Elektro GmbH, Kelheim, Germany). Once nebulization was complete the dispersion was left to stir for about another 60 minutes at room temperature before the encased particles were recovered by vacuum filtration over a Whatman No. 1 filter paper (Whatman Intl. Ltd., Maidstone, Kent, U.K.) The filter cake was rinsed with deionized water, frozen and lyophilized in an Edwards SuperModulyo lyophilizer (Edwards, Crawley, West Sussex, U.K.). The resulting particles were analyzed for particle size using the Malvern Mastersizer/E (Malvern, Worcs., U.K.) and 1 % Tween 20 in water as a dispersant. The resulting particles had a mean particle size (d(0.5)) of 84.75 μm.

VIII(b): Nebulization Using Ethyl Acetate as Solvent and Room-temperature IPA as Non-solvent The nebulization was carried out substantially according to the procedure of Example VIII(a) but using about 0.99 g of cation exchanger of Example I(c) (not bound to polypeptide) dispersed in a 24.88% (W/W) solution of encasing copolymer of Example V(a) in ethyl acetate (Riedel-de Haen, Seelze, Germany) such that the ratio of cation exchanger to encasing copolymer was about 0.96:1 by weight. The resulting particles had a mean particle size (d(0.5)) of 100.56 μm VIII(c): Nebulization Using Ethyl Acetate as Solvent and a Higher Frequency Probe About 1.02 g of cation exchanger of Example I(c) (not bound to polypeptide) was dispersed in a 15.14% (W/W) solution of encasing copolymer of Example V(a) in ethyl acetate (Riedel-de Haen) such that the ratio of cation exchanger to encasing copolymer was about 1.05:1 by weight. This dispersal was achieved by homogenizing with an Ultra-turrax T25 (IKA, Staufen, Germany) at about 9,500 rpm for about 5 minutes.

After dispersal, the dispersion was fed to a Martin Walter 400 GSIP nebulizer (Sodeva, Le Bouget du Lac, France) with an ultrasonic frequency setting of about 34:6 kHz using a ceramic piston pump (FMI, Oyster Bay, N.Y., U.S.A.) set at 5 ml/min flow rate. Upon reaching the nozzle the dispersion was nebulized into IPA (Labscan, Dublin, Ireland) cooled to about −77° by the addition of dry-ice pellets (A.I.G., Dublin, Ireland). This IPA acted as a collecting non-solvent and was stirred at 300 rpm using a Heidolph stirrer (Heidolph Elektro GmbH, Kelheim, Germany). Once nebulization was complete the coated particles were recovered by vacuum filtration over a Whatman No. 1 filter paper (Whatman Intl. Ltd., Maidstone, Kent, U.K.). The filter cake was rinsed with deionized water, frozen and lyophilized in an Edwards SuperModulyo lyophilizer (Edwards, Crawley, West Sussex, U.K.). The resulting particles were analyzed for particle size using the Malvern Masterizer/E (Malvern, Worcs., U.K.) and 1% Tween 20 in water as a dispersant. The resulting particles had a mean particle size (d(0.5)) of 95.69 μm

EXAMPLE IX

Binding to CE's and Subsequent Encasing of Somatostatin Analog Peptides C and D IX(a): Loading with Peptide C About 1.01 g of the sodium salt of Example I(c) dispersed in a solution containing 0.25 g of the free base of peptide C., which has the structure N-hydroxyethylpiperazinyl-acetyl-D-Phe-Cys-Tyr-D-Trp-Lys-Abu-Cys-Thr-$NH_2$ where the two Cys residues are bonded by a disulfide bond (Kinerton Ltd., Dublin, Ireland) dissolved in 40 ml deionized water. The dispersion was incubated with stirring for about 2 hours before filtering over a 9 cm diameter Whatman No. 1 filter paper (Whatman Intl. Ltd., Maidstone, Kent, U.K.). The filter cake was rinsed with further deionized water, frozen, and lyophilized in an Edwards SuperModulyo (Edwards, Crawley, West Sussex. U.K.). The sample was then sent for nitrogen analysis to determine the amount of peptide bound, 20.21%.

IX(b): Loading with Peptide D

Using the procedure of Example IX(a) but using about 204 g of the sodium salt of Example I(c) dispersed in a solution containing 0.51 g of the free base of peptide D, which has the structure N-hydroxyethylpiperazinyl-ethylsulfonyl-Phe-Cys-Tyr-D-Trp-Lys-Abu-Cys-Thr-$NH_2$ where the two Cys residues are bonded by a disulfide bond (Kinerton Ltd., Dublin, Ireland) dissolved in 80 ml. The sample was then sent for nitrogen analysis to determine the amount of peptide bound, 19.53%.

EXAMPLE X

The bound microparticles of Examples IX(a) and IX(b) were encased as described in Example VII yielding the following results:

| Ex. No. | Peptide-loaded CE | Coating copolymer | Conc. (W/W) of coating copolymer in acetonitrile | Coating copolymer: Peptide loaded CE | Mean Particle Size (μm) | Wt. % Peptide Loading |
|---|---|---|---|---|---|---|
| X(a) | IX(a) | V(c) | 12.51% | 1:1 | 83.33 | 9.48% |
| X(b) | IX(b) | V(c) | 12.48% | 0.98:1 | 72.15 | 8.81% |
| X(c) | IX(b) | V(d) | 12.35% | 0.98:1 | 86.03 | 6.14% |

What is claimed is:

1. A process for making an encased bound microparticle or microparticles wherein the encased bound microparticle or microparticles comprise bound microparticle or microparticles and an absorbable encasing polymer where the bound microparticle or microparticles comprise an absorbable heterochain polymer core and one or more peptide, one or more protein or a combination thereof ionically immobilized on said absorbable heterochain polymer core where each peptide is independently selected from growth hormone releasing peptide (GHRP), luteinizing hormone-releasing hormone (LHRH), somatostatin, bombesin, gastrin releasing peptide (GRP), calcitonin, bradykinin, galanin, melanocyte stimulating hormone (MSH), growth hormone releasing factor (GRF), amylin, tachykinins, secretin, parathyroid hormone (PTH), enkaphelin, endothelin, calcitonin gene releasing peptide (CGRP), neuromedins, parathyroid hormone related protein (PTHrP), glucagon, neurotensin, adrenocorticothrophic hormone (ACTH), peptide YY (PYY), glucagon releasing peptide (GLP), vasoactive intestinal peptide (VIP), pituitary adenylate cyclase activating peptide (PACAP), motilin, substance P, neuropeptide Y (NPY), TSH and analogs and fragments thereof or a pharmaceutically acceptable salt thereof; and where each protein is independently selected from growth hormone, erythropoietin, granulocyte-colony stimulating factor, granulocyte-macrophage-colony stimulating factor and interferons;

said process comprising the steps of:

obtaining a dispersion, where the dispersion comprises solid bound microparticles in a solution of the absorbable encasing polymer, by homogenizing and concurrently dispersing said solid bound microparticles into the solution of an absorbable encasing polymer; and nebulizing said dispersion through a nebulization probe into a liquid, non-solvent of said absorbable encasing polymer at a flow rate of about 1 ml/min to 15 ml/min wherein said non-solvent is maintained at a temperature of about room temperature to about −80° C. and said probe has an operating ultrasonic frequency range of 12 kHz to 36 kHz.

2. A process according to claim 1 wherein said medium comprises isopropanol or ethanol.

3. A process according to claim 2 wherein the solution of the absorbable polymer consists of about 5% to 30% of the absorbable polymer.

4. A process according to claim 1 wherein the peptide, peptides, protein or proteins or combination thereof of the bound microparticle comprises 0.1% to 30% of the total mass of the bound microparticle.

5. A process according to claim 4 wherein the absorbable polymer core comprises glycolate units and citrate residues wherein the ratio of glycolate units to citrate residues is about 7-1 to about 20-1 or glycolate units and tartrate residues wherein the ratio of glycolate units to tartrate residues is about 7-1 to about 20-1 or glycolate units and malate residues wherein the ratio of glycolate units to malate residues is about 7-1 to about 20-1.

6. A process according to claim 5 wherein absorbable encasing polymer comprises (a) l-lactide based units and glycolide based units where the ratio of l-lactide based units to glycolide based units is about 60-40 to about 90-10, (b) d,l-lactide based units and glycolide based units where the ratio of d,l-lactide based units to glycolide based units is about 60-40 to about 90-10, (c) d,l-lactide based units, or (d) l-lactide based units and d,l-lactide based units where the ratio of l-lactide based units to d,l-lactide based units is about 80-20.

7. A process according to claim 6 wherein the absorbable encasing polymer constitutes 5 to 70% of the total mass of the encased bound microparticle or microparticles.

8. A process according to claim 7 wherein the absorbable encasing polymer constitutes 20–60% of the total mass of the encased bound microparticle or microparticles.

9. A process according to claim 8 wherein the absorbable encasing polymer constitutes 30–50% of the total mass of the encased bound microparticle or microparticles.

10. A process according to claim 9 where the peptide is an LHRH analog.

11. A process according to claim 10 where the LHRH analog is p-Glu-His-Trp-Ser-Tyr-D-Trp-Leu-Arg-Pro-Gly-$NH_2$.

12. A process according to claim 9 where the peptide is a somatostatin analog.

13. A process according to claim 12 where the somatostatin analog is H-β-D-Nal-Cys-Tyr-D-Trp-Lys-Val-Cys-Thr-$NH_2$, where the two Cys are bonded by a disulfide bond.

14. A process according to claim 12 where the somatostatin analog is N-hydroxyethylpiperazinyl-acetyl-D-Phe-Cys-Tyr-D-Trp-Lys-Abu-Cys-Thr-$NH_2$ where the two Cys residues are bonded by a disulfide bond.

15. A process according to claim 12 where the somatostatin analog is N-hydroxyethylpiperazinyl-ethylsulfonyl-Phe-Cys-Tyr-D-Trp-Lys-Abu-Cys-Thr-$NH_2$ where the two Cys residues are bonded by a disulfide bond.

* * * * *